(12) United States Patent
Pecor et al.

(10) Patent No.: US 9,174,031 B2
(45) Date of Patent: Nov. 3, 2015

(54) DEVICE AND METHOD FOR DEFLATION AND REMOVAL OF IMPLANTABLE AND INFLATABLE DEVICES

(75) Inventors: Robert Pecor, Aliso Viejo, CA (US); Outhit Bouasaysy, Corona, CA (US); Jason Kwok, Anaheim, CA (US); Mark Ashby, Laguna Niguel, CA (US)

(73) Assignee: ReShape Medical, Inc., San Clemente, CA (US)

( * ) Notice: Subject to any disclaimer, the term of this patent is extended or adjusted under 35 U.S.C. 154(b) by 101 days.

(21) Appl. No.: 12/723,545

(22) Filed: Mar. 12, 2010

(65) Prior Publication Data

US 2010/0234853 A1  Sep. 16, 2010

Related U.S. Application Data

(60) Provisional application No. 61/160,207, filed on Mar. 13, 2009, provisional application No. 61/228,081, filed on Jul. 23, 2009, provisional application No. 61/245,630, filed on Sep. 24, 2009.

(51) Int. Cl.
*A61M 29/00* (2006.01)
*A61M 25/10* (2013.01)
(Continued)

(52) U.S. Cl.
CPC .......... *A61M 25/1018* (2013.01); *A61F 5/0089* (2013.01); *A61M 25/0068* (2013.01)

(58) Field of Classification Search
CPC ... A61F 5/0003; A61F 5/0004; A61F 5/0013; A61F 5/0027; A61F 5/003; A61F 5/0083; A61F 5/0086; A61F 5/0089; A61F 5/00; A61F 6/20; A61B 17/00; A61B 17/12136; A61M 25/1018; A61M 25/10184; A61M 25/10185; A61M 25/10186

USPC ................ 606/192; 623/23.65, 23.67; 604/99.01–99.03
See application file for complete search history.

(56) References Cited

U.S. PATENT DOCUMENTS 2,493,326 A   1/1950   Trinder
4,133,315 A   1/1979   Berman et al.
(Continued)

FOREIGN PATENT DOCUMENTS

DE   8708978 U1   11/1987
EP   0103481      3/1984
(Continued)

OTHER PUBLICATIONS

Wahlen CH et al. "The BioEnterics Intragastric Balloon: How to use it" Obesity Surgery 2001;11:524-527.
(Continued)

*Primary Examiner* — David C Eastwood
*Assistant Examiner* — Martin T Ton
(74) *Attorney, Agent, or Firm* — Nicole S. Dunham (57) ABSTRACT

Deflation devices including a catheter having a proximal opening at a proximal end and a distal opening at a distal end, and a coring member disposed within the catheter are disclosed herein. In one embodiment, the coring member comprises a handle disposed near the proximal end of the catheter, a cable, and a coring tip disposed near the distal end of the catheter. The distal end of the catheter can be configured to press against a wall of a balloon to create a substantially normalized surface of the balloon relative to a coring tip. A method for deflating and removing an implanted device, in accordance with another embodiment, can include pressing a distal end of a catheter against the wall of an inflated balloon of the device, and advancing the coring tip within the catheter beyond the distal end of the catheter and into the balloon.

17 Claims, 6 Drawing Sheets

(51) Int. Cl.
*A61F 5/00* (2006.01)
*A61M 25/00* (2006.01)

(56) References Cited

U.S. PATENT DOCUMENTS

| | | | |
|---|---|---|---|
| 4,198,983 A | 4/1980 | Becker et al. | |
| 4,246,893 A | 1/1981 | Berson | |
| 4,356,824 A | 11/1982 | Vazquez | |
| 4,368,739 A | 1/1983 | Nelson, Jr. | |
| 4,416,267 A | 11/1983 | Garren et al. | |
| 4,465,072 A | 8/1984 | Taheri | |
| 4,465,818 A | 8/1984 | Shirahata et al. | |
| 4,485,805 A | 12/1984 | Foster, Jr. | |
| 4,543,089 A | 9/1985 | Moss | |
| 4,598,699 A | 7/1986 | Garren et al. | |
| 4,694,827 A | 9/1987 | Weiner et al. | |
| 4,723,547 A | 2/1988 | Kullas et al. | |
| 4,899,747 A | 2/1990 | Garren et al. | |
| 4,940,458 A * | 7/1990 | Cohn | 604/512 |
| 5,073,347 A | 12/1991 | Garren et al. | |
| 5,084,061 A | 1/1992 | Gau et al. | |
| 5,123,840 A | 6/1992 | Nates | |
| 5,234,454 A | 8/1993 | Bangs | |
| 5,259,399 A | 11/1993 | Brown | |
| 5,263,934 A | 11/1993 | Haak | |
| 5,273,536 A | 12/1993 | Savas | |
| 5,318,530 A | 6/1994 | Nelson, Jr. | |
| 5,334,187 A | 8/1994 | Fischell et al. | |
| 5,431,173 A | 7/1995 | Chin et al. | |
| 5,496,271 A | 3/1996 | Burton et al. | |
| 5,516,812 A | 5/1996 | Chu et al. | |
| 5,575,772 A | 11/1996 | Lennox | |
| 5,639,810 A | 6/1997 | Smith et al. | |
| 5,643,209 A | 7/1997 | Fugoso et al. | |
| 5,730,722 A | 3/1998 | Wilk | |
| 5,779,728 A | 7/1998 | Lunsford et al. | |
| 5,857,991 A | 1/1999 | Grothoff et al. | |
| 5,876,376 A | 3/1999 | Schwab et al. | |
| 5,938,669 A | 8/1999 | Klaiber et al. | |
| 5,976,073 A | 11/1999 | Ouchi | |
| 5,993,473 A | 11/1999 | Chan et al. | |
| 5,997,503 A | 12/1999 | Willis et al. | |
| 6,149,621 A | 11/2000 | Makihara | |
| 6,179,878 B1 | 1/2001 | Duerig et al. | |
| 6,254,355 B1 | 7/2001 | Gharib | |
| 6,276,567 B1 | 8/2001 | Diaz et al. | |
| 6,280,411 B1 | 8/2001 | Lennox | |
| 6,423,058 B1 | 7/2002 | Edwards et al. | |
| 6,427,089 B1 | 7/2002 | Knowlton | |
| 6,454,785 B2 | 9/2002 | De Hoyos Garza | |
| 6,524,234 B2 | 2/2003 | Ouchi | |
| 6,535,764 B2 | 3/2003 | Imran et al. | |
| 6,540,789 B1 | 4/2003 | Silverman et al. | |
| 6,547,788 B1 | 4/2003 | Maguire et al. | |
| 6,579,301 B1 | 6/2003 | Bales et al. | |
| 6,592,552 B1 | 7/2003 | Schmidt | |
| 6,613,018 B2 | 9/2003 | Bagga et al. | |
| 6,613,037 B2 | 9/2003 | Khosravi et al. | |
| 6,689,051 B2 | 2/2004 | Nakada et al. | |
| 6,706,010 B1 | 3/2004 | Miki et al. | |
| 6,746,460 B2 | 6/2004 | Gannoe et al. | |
| 6,826,428 B1 | 11/2004 | Chen et al. | |
| 6,850,128 B2 | 2/2005 | Park | |
| 6,866,657 B2 | 3/2005 | Shchervinsky et al. | |
| 6,869,431 B2 | 3/2005 | Maguire et al. | |
| 6,890,300 B2 | 5/2005 | Lloyd et al. | |
| 6,890,346 B2 | 5/2005 | Ganz et al. | |
| 6,902,535 B2 | 6/2005 | Eberhart et al. | |
| 6,923,754 B2 | 8/2005 | Lubock | |
| 6,931,286 B2 | 8/2005 | Sigg et al. | |
| 6,939,299 B1 | 9/2005 | Petersen et al. | |
| 6,942,680 B2 | 9/2005 | Grayzel et al. | |
| 6,958,052 B1 | 10/2005 | Charlton | |
| 6,981,980 B2 * | 1/2006 | Sampson et al. | 606/192 |
| 7,001,419 B2 | 2/2006 | DiCaprio et al. | |
| 7,016,735 B2 | 3/2006 | Imran et al. | |
| 7,020,531 B1 | 3/2006 | Colliou et al. | |
| 7,033,373 B2 | 4/2006 | de la Torre et al. | |
| 7,056,305 B2 | 6/2006 | Garza Alvarez | |
| 7,076,305 B2 | 7/2006 | Imran et al. | |
| 7,081,125 B2 | 7/2006 | Edwards et al. | |
| 7,131,945 B2 | 11/2006 | Fink et al. | |
| 7,483,746 B2 | 1/2009 | Lee et al. | |
| 7,625,355 B2 | 12/2009 | Yu | |
| 7,749,254 B2 | 7/2010 | Sobelman et al. | |
| 7,931,693 B2 | 4/2011 | Binmoeller | |
| 8,083,757 B2 | 12/2011 | Gannoe et al. | |
| 2001/0022988 A1 | 9/2001 | Schwarz et al. | |
| 2001/0037127 A1 | 11/2001 | De Hoyos Garza | |
| 2002/0055757 A1 | 5/2002 | Torre et al. | |
| 2002/0107515 A1 | 8/2002 | Edwards et al. | |
| 2002/0161388 A1 | 10/2002 | Samuels et al. | |
| 2002/0173804 A1 | 11/2002 | Rousseau | |
| 2003/0105800 A1 | 6/2003 | Cullen | |
| 2003/0114878 A1 | 6/2003 | Diederich et al. | |
| 2003/0171768 A1 | 9/2003 | McGhan | |
| 2003/0187390 A1 | 10/2003 | Bates et al. | |
| 2004/0044354 A1 | 3/2004 | Gannoe et al. | |
| 2004/0059289 A1 | 3/2004 | Garza Alvarez | |
| 2004/0059290 A1 | 3/2004 | Palasis | |
| 2004/0073162 A1 | 4/2004 | Bleam et al. | |
| 2004/0087902 A1 | 5/2004 | Richter | |
| 2004/0093058 A1 | 5/2004 | Cottone et al. | |
| 2004/0106899 A1 | 6/2004 | McMichael et al. | |
| 2004/0116897 A1 | 6/2004 | Aboul-Hosn | |
| 2004/0127915 A1 | 7/2004 | Fleenor et al. | |
| 2004/0186502 A1 | 9/2004 | Sampson et al. | |
| 2004/0220665 A1 | 11/2004 | Hossainy et al. | |
| 2004/0236280 A1 | 11/2004 | Rice et al. | |
| 2004/0236361 A1 * | 11/2004 | Sakurai | 606/167 |
| 2004/0254600 A1 | 12/2004 | Zarbatany et al. | |
| 2005/0027283 A1 | 2/2005 | Richard et al. | |
| 2005/0027313 A1 | 2/2005 | Shaker | |
| 2005/0038415 A1 | 2/2005 | Rohr et al. | |
| 2005/0055039 A1 | 3/2005 | Burnett et al. | |
| 2005/0059990 A1 | 3/2005 | Ayala et al. | |
| 2005/0075624 A1 | 4/2005 | Miesel | |
| 2005/0085792 A1 | 4/2005 | Gershowitz | |
| 2005/0119674 A1 | 6/2005 | Gingras | |
| 2005/0131442 A1 * | 6/2005 | Yachia et al. | 606/185 |
| 2005/0143784 A1 | 6/2005 | Imran | |
| 2005/0159769 A1 | 7/2005 | Alverdy | |
| 2005/0177103 A1 | 8/2005 | Hunter et al. | |
| 2005/0192615 A1 | 9/2005 | Torre et al. | |
| 2005/0267595 A1 | 12/2005 | Chen et al. | |
| 2005/0267596 A1 | 12/2005 | Chen et al. | |
| 2005/0273060 A1 | 12/2005 | Levy et al. | |
| 2006/0058829 A1 | 3/2006 | Sampson et al. | |
| 2006/0178691 A1 | 8/2006 | Binmoeller | |
| 2006/0184112 A1 | 8/2006 | Horn et al. | |
| 2006/0259020 A1 | 11/2006 | Sharratt | |
| 2007/0016262 A1 | 1/2007 | Gross et al. | |
| 2007/0078476 A1 | 4/2007 | Hull et al. | |
| 2007/0093728 A1 * | 4/2007 | Douglas et al. | 600/583 |
| 2007/0100367 A1 | 5/2007 | Quijano | |
| 2007/0100368 A1 | 5/2007 | Quijano | |
| 2007/0100369 A1 | 5/2007 | Cragg | |
| 2007/0135829 A1 | 6/2007 | Paganon | |
| 2007/0142770 A1 | 6/2007 | Rioux et al. | |
| 2007/0149994 A1 | 6/2007 | Sosnowski | |
| 2007/0173881 A1 | 7/2007 | Birk et al. | |
| 2007/0233161 A1 | 10/2007 | Weller et al. | |
| 2007/0250020 A1 | 10/2007 | Kim et al. | |
| 2007/0265369 A1 | 11/2007 | Muratoglu et al. | |
| 2007/0265598 A1 | 11/2007 | Karasik | |
| 2007/0288033 A1 * | 12/2007 | Murature et al. | 606/106 |
| 2008/0082056 A1 | 4/2008 | Mauch et al. | |
| 2008/0085887 A1 | 4/2008 | Didiuk et al. | |
| 2008/0097513 A1 | 4/2008 | Kaji et al. | |
| 2008/0119729 A1 | 5/2008 | Copa et al. | |
| 2008/0172079 A1 | 7/2008 | Birk | |
| 2008/0190363 A1 | 8/2008 | Chen et al. | |
| 2008/0208135 A1 | 8/2008 | Annunziata | |
| 2008/0208241 A1 | 8/2008 | Weiner et al. | |

(56) References Cited

U.S. PATENT DOCUMENTS

| | | |
|---|---|---|
| 2008/0233167 A1 | 9/2008 | Li et al. |
| 2008/0243071 A1 | 10/2008 | Quijano |
| 2008/0243166 A1 | 10/2008 | Paganon et al. |
| 2008/0255601 A1 | 10/2008 | Birk |
| 2008/0312679 A1 | 12/2008 | Hardert et al. |
| 2008/0319471 A1 | 12/2008 | Sosnowski |
| 2009/0048624 A1 | 2/2009 | Alverdy |
| 2009/0259236 A2 | 10/2009 | Burnett et al. |
| 2009/0275973 A1 | 11/2009 | Chen et al. |
| 2010/0023047 A1 | 1/2010 | Simpson |
| 2010/0130998 A1 | 5/2010 | Alverdy |
| 2010/0243135 A1 | 9/2010 | Pepper et al. |
| 2010/0251837 A1 | 10/2010 | Bouasaysy et al. |
| 2011/0178544 A1 | 7/2011 | Sosnowski et al. |
| 2012/0271336 A1 | 10/2012 | Hamman et al. |
| 2012/0289992 A1 | 11/2012 | Quijano et al. |

FOREIGN PATENT DOCUMENTS

| | | |
|---|---|---|
| EP | 0 457 456 | 5/1990 |
| EP | 0 485 903 | 8/1991 |
| EP | 1781183 | 5/2007 |
| FR | 2862525 A1 | 5/2005 |
| FR | 2892297 | 4/2007 |
| GB | 2090747 | 7/1982 |
| GB | 2 139 902 A | 11/1984 |
| JP | S57168674 | 10/1982 |
| JP | 64-015063 A | 1/1989 |
| JP | S6415063 | 1/1989 |
| JP | H091872 | 4/1989 |
| JP | H08322943 | 12/1996 |
| JP | 2001128985 | 5/2001 |
| JP | 2006333888 | 12/2006 |
| WO | WO9000369 | 1/1990 |
| WO | WO9925418 | 5/1999 |
| WO | WO-0141700 | 6/2001 |
| WO | WO-0166166 A2 | 9/2001 |
| WO | WO 2006035446 | 4/2006 |
| WO | WO-2006056944 A1 | 6/2006 |
| WO | WO 2006/128978 | 12/2006 |
| WO | WO-2007027812 | 3/2007 |
| WO | WO-2007053556 A1 | 5/2007 |
| WO | WO-2007053706 A1 | 5/2007 |
| WO | WO-2007053707 A1 | 5/2007 |
| WO | WO-2007075810 A1 | 7/2007 |
| WO | WO-2008042819 A2 | 4/2008 |
| WO | WO-2008121831 A1 | 10/2008 |
| WO | WO-2009055386 A2 | 4/2009 |
| WO | WO-2009112786 A2 | 9/2009 |
| WO | WO-2010048021 | 4/2010 |
| WO | WO-2010115161 A2 | 10/2010 |
| WO | WO-2011011629 A2 | 1/2011 |
| WO | WO-2011011741 A2 | 1/2011 |
| WO | WO-2011011743 A2 | 1/2011 |
| WO | WO-2011038270 A2 | 3/2011 |
| WO | WO2011024077 | 8/2011 |
| WO | WO2011097637 | 8/2011 |
| WO | WO2011127205 | 10/2011 |
| WO | WO-2012048226 A1 | 4/2012 |

OTHER PUBLICATIONS

Patient information "Living with the BIB" by INAMED Health (2004).

International Search Report; International Application No. PCT/US2008/058677, Applicant: ReShape Medical et al., Mailing Date Aug. 21, 2008, 12 pages.

International Search Report; International Application No. PCT/US2006/042710, Applicant: Abdominus, Inc. et al., Mailing Date Mar. 15, 2007, 9 pages.

International Search Report; International Application No. PCT/US2006/048647, Applicant: Abdominus, Inc. et al., Mailing Date May 22, 2007, 12 pages.

International Search Report; International Application No. PCT/US2008/068058, Applicant: ReShape Medical, Inc. et al, Mailing Date Nov. 19, 2008, 11 pages.

International Search Report; International Application No. PCT/US2006/042711, Applicant: Abdominus, Inc. et al, Mailing Date Mar. 16, 2007, 9 pages.

Supplementary European Search Report for EP 03726447.0, mailed Mar. 1, 2006.

International Search Report; International Application No. PCT/US2003/012782, Applicant: Applied Medical Resources Corporation, Mailing Date Oct. 28, 2003, 7 pages.

International Search Report; International Application No. PCT/US2010/029865, Applicant: ReShape Medical, Inc., Mailing Date Jan. 5, 2011, 9 pages.

Final Office Action; U.S. Appl. No. 11/694,536, Mailing Date Mar. 11, 2011, 13 pages.

International Search Report; International Application No. PCT/US2011/024082, Applicant: ReShape Medical, Inc., Mailing Date Apr. 6, 2011, 10 pages.

International Search Report; International Application No. PCT/US2011/024077; Applicant: ReShape Medical. Inc., Mailing Date Apr. 6, 2011, 12 pages.

International Search Report; International Application No. PCT/US2010/042948; Applicant: ReShape Medical, Inc., Mailing Date Apr. 1, 2011, 11 pages.

International Search Report; International Application No. PCT/US2010/043136; Applicant: ReShape Medical, Inc., Mailing Date Apr. 12, 2011, 9 pages.

International Search Report; International Application No. PCT/US2010/043134; Applicant: ReShape Medical, Inc., Mailing Date Apr. 27, 2011, 12 pages.

International Search Report; International Application No. PCT/US2011/0426233; Applicant: ReShape Medical, Inc., Mailing Date Apr. 26, 2011, 9 pages.

"ReShape Inflatable Gastric Ballon Going on Trial as Weight Loss Option," MedGadget: Internet Journal of Emerging Medical Technologies. Feb. 4, 2010. (5 pages).

European Supplementary Search Report; EP Application No. 10802918.2, Applicant: ReShape Medical, Inc., mailed Jun. 5, 2013, 6 pgs.

European Supplementary Search Report; EP Application No. 10802994.3, Applicant: ReShape Medical, Inc., mailed Jun. 28, 2013, 8 pgs.

Non-Final Office Action; U.S. Appl. No. 11/263,302; dated: Oct. 9, 2012, 6 pages.

Non-Final Office Action; U.S. Appl. No. 12/625,473; dated Jul. 12, 2012; 10 pages.

Non-Final Office Action; U.S. Appl. No. 12/753,751; dated Oct. 5, 2012, 8 pages.

Non-Final Office Action; U.S. Appl. No. 13/074,956; dated Oct. 1, 2012, 8pages.

Final Office Action; U.S. Appl. No. 11/768,152, Mailing Date Jan. 19, 2011, 13 pages.

International Search Report; International Application No. PCT/US2010/050260; Applicant: ReShape Medical, Inc., Mailing Date: Jun. 17, 2011, 9 pages.

International Search Report; International Application No. PCT/US2011/031463; Applicant: ReShape Medical, Inc., Mailing Date: Jun. 27, 2011, 10 pages.

International Search Report; International Application No. PCT/US2006/042336, Applicant: Abdominus, Inc., Mailing Date Mar. 14, 2007, 9 pages.

International Search Report; International Application No. PCT/US2011/024077; Applicant: ReShape Medical, Inc., Mailing Date Apr. 6, 2011, 12 pages.

International Search Report and Written Opinion; International Application No. PCT/US1155373, Applicant: Reshape Medical, Inc., Mailing Date Jan. 20, 2012, 7 pages.

Non-Final Office Action; U.S. Appl. No. 12/625,473; Mailing Date Oct. 24, 2011, 18 pages.

Extended European Search Report; Application No. EP11766679.2, Applicant: Reshape Medical. Inc., mailed Dec. 12, 2013, 6 pages.

(56) References Cited

OTHER PUBLICATIONS

Final Office Action; U.S. Appl. No. 13/858,767, Mailing Date May 22, 2013, 12 pages.
International Search Report; International Application No. PCT/US2011/024082, Applicant: ReShape Medical, Inc., dated: Apr. 6, 2011, 10 pages.
Extended European Search Report; Application EP11740536.5, Applicant: ReShape Medical, Inc., mailed Jul. 3, 2014, 8 pages.
Extended European Search Report; Application EP11831683.5, Applicant: Reshape Medical, Inc., mailed Jul. 3, 2014, 8 pages.
Final Office Action; U.S. Appl. No. 13/556,032, mailed on Jan. 28, 2014, 8 pages.
Non-Final Office Action: U.S. Appl. No. 13/386,650; mailed on Jun. 3, 2014, 15 pages.
Notice of Allowance: U.S. Appl. No. 12/753,803, dated May 13, 2014, 18 pages.
Ostrovsky, ReShape Inflatable Gastric Balloon going on Trial as Weight Loss Option: http://www.medgadget.com/2010/02/reshape_inflatable_gastric_balloon_system_going_on_trial_as_weight_loss_option.html Feb. 4, 2010, retrieved on Feb. 2010-Feb. 2013.
Extended European Search Report; Application No. EP6827098.3, Applicant: Reshape Medical, Corporation, mailed on Aug. 25, 2014, 3 pages.
Extended European Search Report; Application No. EP6827314.3, Applicant: ReShape Medical Corporation, mailed Aug. 1, 2014, 3 pages.
Extended European Search Report; Application No. EP6827313.5, Applicant: ReShape Medical Corporation, mailed Jul. 30, 2014, 5 pages.
Extended European Search Report; Application No. EP6847847.8, Applicant: ReShape Medical Corporation, mailed Aug. 14, 2014, 5 pages.
Final Office Action; U.S. Appl. No. 13/858,767, mailed on May 30, 2014, 12 pages.
Non-Final Office Action: U.S. Appl. No. 13/386,638, mailed on Jun. 27, 2014, 12 pages.
Extended European Search Report; Application No. EP11748141.6, Applicant: Reshape Medical, Inc., mailed Feb. 25, 2014, 6 pages.
Extended European Search Report; Application No. EP11766679.2, Applicant: Reshape Medical, Inc., mailed Dec. 12, 2013, 6 pages.
Extended European Search Report; Application No. 08732989.2, Applicant: Reshape Medical, Inc., mailed Oct. 16, 2014, 7 pages.
Final Rejection; U.S. Appl. No. 13/556,032, mailed on Apr. 28, 2015, 9 pages.
Non-Final Office Action; U.S. Appl. No. 13/074,956; dated Apr. 27, 2015, 8 pages.
Final Office Action; U.S. Appl. No. 13/386,650; mailed on Apr. 6, 2015, 15 pages.
Non-Final Office Action; U.S. Appl. No. 13/577,601, mailed Jan. 8, 2015, 14 pages.
Non-Final Office Action; U.S. Appl. No. 13/577,612, mailed Jan. 8, 2015, 13 pages.
Non-Final Office Action; U.S. Appl. No. 13/858,767, mailed Jan. 16, 2015, 14 pages.
European Examination Report; Application No. EP108002918.2, Applicant: Reshape Medical Inc., mailed Dec. 17, 2014, 5 pages.
European Examination Report; Application No. EP108029943, Applicant: Reshape Medical Inc., mailed Dec. 18, 2014, 4 pages.
Japanese Office Action; Application No. 2013-43712, mailed Jan. 8, 2015, 8 pages.
Canadian Office Action; Application No. 2,638,988, mailed Dec. 22, 2014, 3 pages.
Japanese Office Action; Application No. 2014-52972; mailed Feb. 25, 2015, 7 pages.
Canadian Office Action; Application No. 2,691,530, mailed Dec. 18, 2014, 4 pages.
Canadian Office Action; Application No. 2638163, mailed Mar. 10, 2015, 4 pages.
European Supplementary Search Report; Application No. 08771842.5, Apr. 4, 2015, 3 pages.
European Examination Reported; Application No. 08771842.5, May 7, 2015, 5 pages.
Non-Final Office Action; U.S. Appl. No. 13/639,483, mailed on May 21, 2015, 8 pages.
Notice of Allowance; U.S. Appl. No. 13/577,618, mailed May 29, 2015, 7 pages.
Non-Final Rejection; U.S. Appl. No. 13/386,647, mailed Apr. 30, 2015, 15 pages.
Notice of Allowance; U.S. Appl. No. 13/386,638, mailed Feb. 11, 2015, 6 pages.
Canadian Office Action; Application No. CA 2680124, Applicant: ReShape Medical Corporation, mailed Nov. 4, 2014, 3 pages.
Canadian Office Action; Application No. CA 2638988, Applicant ReShape Medical Corporation, mailed Mar. 6, 2014, 4 pages.
Canadian Office Action; Application No. CA 2638989, Applicant: ReShape Medical Corporation, mailed May 22, 2013 3 pages.
Canadian Office Action; Application No. CA 2640554, Applicant: ReShape Medical Corporation, mailed May 27, 2013, 2 pages.
Canadian Office Action; Application No. CA2484838, Applicant: ReShape Medical, Inc., mailed Nov. 13, 2009, 3 pages.
Canadian Office Action; Application No. CA2484838, Applicant: ReShape Medical, Inc., mailed Sep. 24, 2010, 3 pages.
Canadian Office Action; Application No. CA2638163, Applicant: ReShape Medical Corporation, mailed Jul. 17, 2013, 2 pages.
Canadian Office Action; Application No. CA2638988, Applicant: ReShape Medical Corporation, mailed May 28, 2013, 3 pages.
Canadian Office Action; Application No. CA2780085, Applicant: ReShape Medical, Inc., mailed Jul. 23, 2012, 2 pages.
European Examination Report; Application No. 03726447.0, Applicant: Applied Medical Resources Corporation: Oct. 26, 2007, 4 pages.
Japanese Final Office Action; Application No. JP2013-043712, mailed Nov. 15, 2013, 5 pages.
Japanese Office Action; Application No. 2013-142327, mailed May 29, 2014, 4 pages.
Japanese Office Action; Application No. JP2010-501261, mailed Sep. 7, 2012, 10 pages.
Japanese Office Action; Application No. JP2010-515040, mailed Jan. 7, 2013, 18 pages.
Japanese Office Action; Application No. JP2012-503759, mailed Mar. 24, 2014, 5 pages.
Japanese Office Action; Application. No. JP2013-043712, mailed Apr. 22, 2013, 5 pages.

* cited by examiner

DEVICE AND METHOD FOR DEFLATION AND REMOVAL OF IMPLANTABLE AND INFLATABLE DEVICES

RELATED APPLICATIONS

This application claims the full Paris Convention benefit of and priority to U.S. Provisional Patent Application Ser. No. 61/160,207, filed Mar. 13, 2009; U.S. Provisional Patent Application Ser. No. 61/228,081, filed Jul. 23, 2009; and U.S. Provisional Patent Application Ser. No. 61/245,630, filed Sep. 24, 2009, the contents of which are incorporated by reference herein in their entirety, as if fully set forth herein.

This application incorporates by reference U.S. Pat. Pub. No. 2007/0100368, published May 3, 2007; U.S. Pat. Pub. No. 2007/0100369, published May 3, 2007; U.S. Pat. Pub. No. 2007/0149994, published Jun. 28, 2007; WIPO Pub. No. WO 2007/053556, published Oct. 5, 2007; WIPO Pub. No. WO 2007/053707, published Oct. 5, 2007; WIPO Pub. No. WO 2007/053706, published Oct. 5, 2007; and WIPO Pub. No. WO 2007/075810, published May 7, 2007; each as if fully set forth herein in its entirety.

FIELD OF THE INVENTION

This disclosure relates generally to maintenance of implantable, inflatable devices. In particular, the present invention relates to a device and method for deflation and removal of implantable gastric devices.

SUMMARY

According to embodiments, disclosed is a method for deflating and removing an implantable, inflatable device comprising: pressing a distal end of a catheter against the wall of an inflated balloon of an implanted device; advancing the coring tip within the catheter beyond the distal end of the catheter and into the balloon, whereby a hole adapted for advancing the catheter is created in the wall of the balloon; and advancing the catheter into the balloon. The method may further comprise retracting the coring device from within the balloon or removing the contents of the balloon through the catheter.

Pressing the distal end of the catheter against the wall of the balloon may create a substantially normalized surface of the balloon relative to the coring tip. The coring tip may be advanced into the balloon while applying a pressure lower than the pressure inside the balloon at the point of contact between the distal end of the catheter and the wall of the balloon. The coring tip may also be advanced into the balloon while rotating the coring tip or while applying longitudinal and/or rotational oscillation to the coring tip. The longitudinal and/or rotational oscillation may be applied at a frequency in the ultrasound range. The coring tip may also be advanced into the balloon while applying an energy, such as RF hi-frequency electrical energy to the coring tip.

According to embodiments, disclosed is a deflation device including a catheter having a proximal opening at a proximal end and a distal opening at a distal end; and a coring member disposed within the catheter and comprising a handle disposed near the proximal end of the catheter, a cable, and a coring tip disposed near the distal end of the catheter; wherein the coring tip is a sharpened, hollow cylinder. The device may further comprise at least a luer connector assembly disposed adjacent to the proximal end of the catheter.

The coring tip may be configured to puncture a wall of a balloon when pressed against a portion of the wall of the balloon. The distal end of the catheter may be configured to be pressed against a portion of the wall of the balloon without puncturing the wall of the balloon. The catheter may have an inner diameter of between about 0.060 inches and about 0.085 inches, and an outer diameter of between about 0.080 inches and about 0.125 inches. The coring tip may have an inner diameter of between about 0.030 inches and about 0.045 inches and an outer diameter of between about 0.040 inches and about 0.065 inches. The cable may be configured to transfer to the coring tip at least one of torque, tension, and compression applied to the handle.

According to embodiments, disclosed is a kit, comprising: a catheter having a proximal opening at a proximal end and a distal opening at a distal end; and a coring member disposed within the catheter and comprising a handle disposed near the proximal end of the catheter, a cable, and a coring tip disposed near the distal end of the catheter; wherein the coring tip may be a sharpened, hollow cylinder; and directions for use.

DRAWINGS

The above-mentioned features and objects of the present disclosure will become more apparent with reference to the following description taken in conjunction with the accompanying drawings wherein like reference numerals denote like elements and in which.

DETAILED DESCRIPTION

Medical devices for the treatment of obesity are available. Such devices entail a single or multiple balloon system that is implanted in the stomach, inter alia. These balloons may be made of silicone or other bio-compatible substances and are filled with saline solution as part of the implantation process. After a clinically designated or otherwise desired implant period within the stomach, it is desirable to pierce the balloon wall so that the balloon contents can be evacuated, such as by aspiration.

Due to a combination of balloon system design, degradation of the balloon material physical properties, and the nature of conventional beveled or conical piercing tips, the balloons frequently tear or rupture when the tip is advanced into the balloon wall. Fluid collects in the stomach as it escapes from the torn or ruptured balloon. This fluid then needs to be evacuated via the endoscope and adds time and complexity to the procedure. There is also an increased risk of fluid aspirating into the trachea, causing breathing difficulties for the patient. Additionally, when the balloon tears or ruptures, the piercing tip or its surrounding catheter cannot be used to fully vacuum out the fluid in the balloon. This leads to additional work removing the balloons, as the user is required to cut or tear drains in the balloon wall, such as by scissors or other suitable means, so that any retained fluid or air in the balloon is released, preventing unwanted drag in the esophagus during removal of the device.

Conventional piercing catheters such as the Cook Medical Baron™ brand of aspiration needle are composed of two members and are advanced down an endoscope into the stomach with the inner member retracted. Under direct endoscopic visualization, the inner member is advanced to expose the beveled piercing tip and the entire device is pushed forward to puncture the balloon. This often results in a tear or rupture of balloons.

Another intragastric balloon removal device, such as the Balloon Extraction Set™ (BES) manufactured by Aprime Medical and Surgical Supplies, is composed of two members: the outer member is a simple tubular catheter and the inner member is a wire with a conical piercing tip. This device is advanced down an endoscope into the stomach with the inner member retracted so that the piercing tip is concealed within the tip of the outer catheter. Under direct endoscopic visualization, the BES is advanced out of the endoscope, the inner piercing member is exposed, and the device is pushed forward into the balloon wall to pierce it. This also often results in a tear or rupture of balloons.

It has been observed that devices, such as the BES, have relatively high surface friction and poor stretch resistance. As a result, maneuverability of the device is compromised and the outer catheter stretches to the point that it covers the tip of the inner member and the device cannot be used to puncture the balloon.

According to embodiments of the present disclosure, devices and methods are provided to make a cored opening in the form of a small hole in the wall of an inflated balloon with a coring member, and advance an outer catheter into the opening with the opening forming a seal around the outer catheter. Then, with the coring member removed, the fluid within the balloon may be evacuated using a vacuum on the proximal end of the outer catheter.

Figure 1:
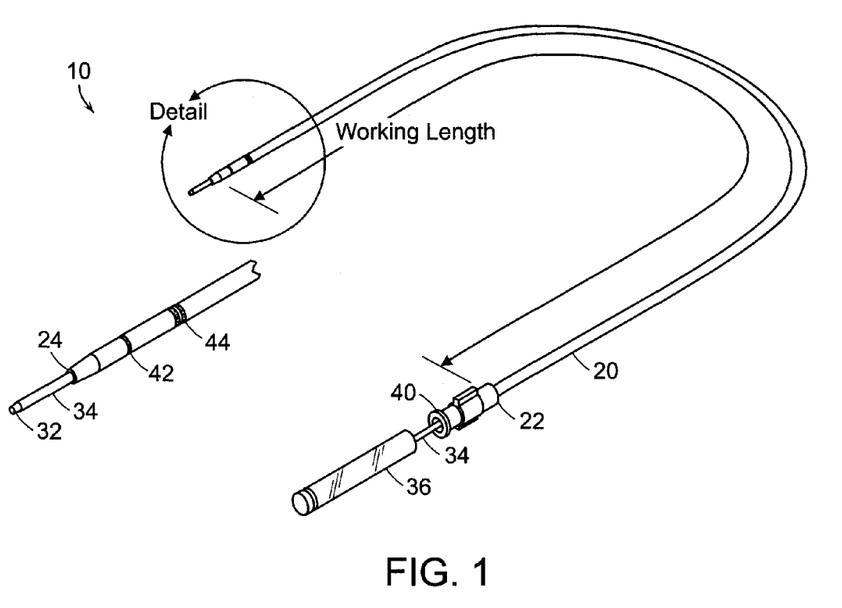
FIG. 1 is a plan and schematic view of embodiments of a device for deflation and removal of an implantable gastric device, according to illustrative aspects of the present disclosure.

Referring to FIG. 1, those skilled in the art readily understand an illustrative, and not limiting, example is shown. Scale issues are obviated by the need for illustration, and not intended to be limiting. A deflation device 10 may include a catheter 20, having a proximal end 22 and a distal end 24, and a coring member comprising a coring tip 32, a cable 34, and a handle 36.

Catheter 20 may comprise a single-lumen tube. A female luer connector 40 may be affixed to proximal end 22. Catheter 20 may have markings 42 and 44 near the distal end 24. The markings may each indicate a distance from the distal end 24 as a reference during use of the device 10. Catheter 20 may have a square-cut distal end 24 and may have a tapered distal section extending from distal end 24, as shown in FIG. 1.

According to embodiments, coring tip 32 may be a square-cut, hypo tube with a sharp distal edge. Cable 34 may comprise a wire rope core, solid stylet, or a cable such as the Helical Hollow Strand™ by Fort Wayne Metals®, of Fort Wayne, Ind. Cable 34 may be designed to transfer tension, compression, and torque without kinking or whipping. Cable 34 may be attached to a proximal hypo tube that is attached to handle 36, disposed at the proximal end 22 of catheter 20. The coring member may be configured to travel within catheter 20, such that coring tip 32 may be retracted within the catheter or extended beyond the distal end 24 of catheter 20.

According to embodiments, coring tip 32 provides a hole-making element instead of a beveled or conical piercing tip. Coring tip 32 may be a sharpened, hollow cylinder. Coring tip 32 may puncture a balloon without causing a tear, leak, or rupture at the point of puncture. Beveled or conical piercing tips create stress concentrations and tear propagation points when the balloon is pierced. This stress concentration is further exacerbated when the pierced opening is stretched greatly to accommodate the outer catheter's outer diameter. Coring tip 32 may cut a smooth and circular hole in the balloon, which creates a smooth and symmetric opening that dramatically reduces the possibility of tear propagation points and stress concentrations. Coring tip 32 also creates a larger opening for catheter 20 to be inserted without significant stretching of the opening to accommodate catheter 20. These outcomes combine to allow for a consistent balloon puncture with minimal risk of tear, rupture, or not sealing around catheter 20. Catheter 20 may be designed to provide low surface friction with respect to the coring member. Catheter 20 may further be designed to provide resistance to stretching.

Catheter 20 may be designed to provide low surface friction with respect to the endoscope lumen that the catheter is delivered through. This may be achieved by covering the catheter's outer surface with a Teflon jacket or a hydrophilic coating. Catheter 20 may further designed to provide resistance to stretching by reinforcing the catheter tubing with a stainless steel or nitinol braid.

Catheter 20 may be configured to be delivered and operated through the working channel of a flexible endoscope, for example with a channel length of at most about 57 inches and minimum channel diameter of about 2.8 mm.

According to certain embodiments and prototypes, coring tip 32 may have an outer diameter slightly smaller than the outer diameter of catheter 20. For example, catheter 20 may have an inner diameter of between about 0.060 inches and about 0.085 inches, and an outer diameter of between about 0.080 inches and about 0.125 inches. Catheter 20 may have a length of between about 25 inches and about 75 inches. Coring tip 32 may have an inner diameter of between about 0.030 inches and about 0.045 inches and an outer diameter of between about 0.040 inches and about 0.065 inches. For example, catheter 20 may have an inner diameter of about 0.073 inches and an outer diameter of about 0.103 inches. Catheter 20 may have a length of about 63 inches. Coring tip 32 may have an inner diameter of about 0.040 inches and an outer diameter of about 0.052 inches. The result is a cored opening of a balloon that wraps around the outer wall of catheter 20 and forms a leak-proof seal during the fluid removal procedure, and facilitates the complete evacuation of the contents of the balloon through catheter 20.

According to embodiments, luer connector 40 of catheter 20 may be a standard luer adaptor or connector. According to embodiments, luer connector 40 may be threaded on its inner surface, and handle 36 may include threading or other extensions on its outer surface, such that handle 36 mates with luer connector 40. According to embodiments, the threaded mating between handle 36 and luer connector 40 may allow a user to thread handle 36 into luer connector 40, which would simultaneously apply torque (rotation) and longitudinal force on coring tip 32. According to embodiments, threaded mating between handle 36 and luer connector 40 may also help maintain the coring member's position relative to catheter 20, such that travel of coring tip 32 within catheter 20 may be limited, thereby reducing the wear on coring tip 32 against the inner walls of catheter 20. According to embodiments, such threading, extensions, or other channels that regulate the rotational or axial movements of the coring member and coring tip 32 may be provided along any portion of catheter 20 or the coring member.

According to embodiments, the coring member may include a device to provide rotation and advancement of coring tip 32. Such a mechanism could be either electrically powered, mechanically powered (such as spring loaded), manually powered, or combinations thereof.

Figure 2A:
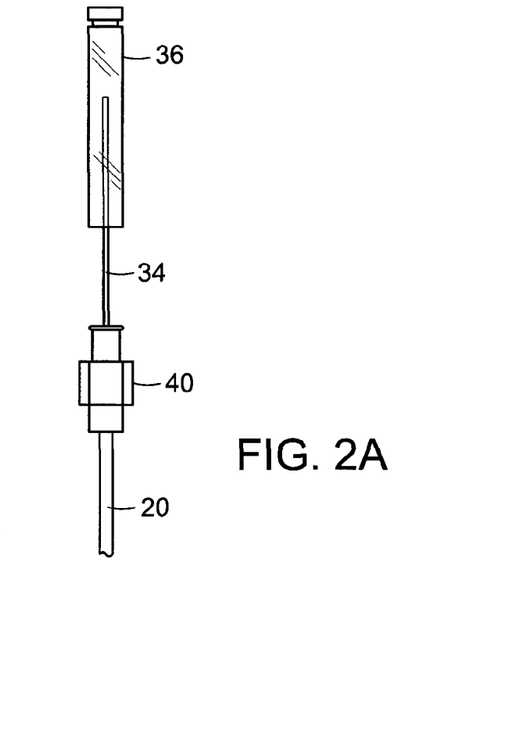
FIG. 2A is a view of embodiments of a proximal portion of a deflation device during approach toward a balloon, according to illustrative aspects of the present disclosure.
Figure 2B:
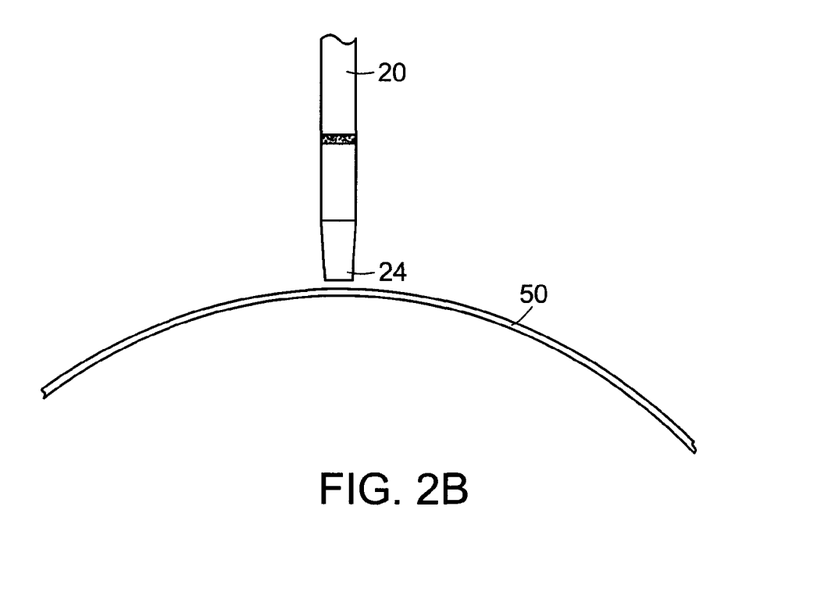
FIG. 2B is a view of embodiments of a distal portion of a deflation device during approach toward a balloon, according to illustrative aspects of the present disclosure.
Figure 3:
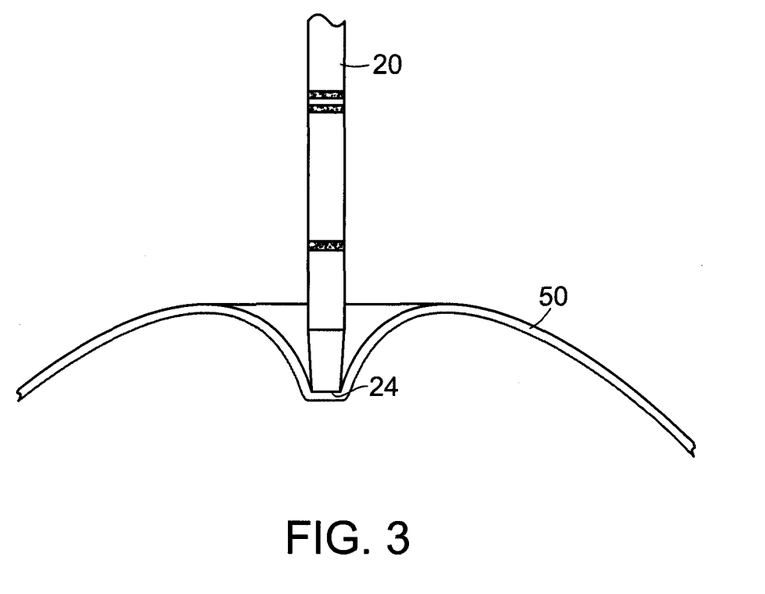
FIG. 3 is a view of embodiments of a distal portion of a deflation device pressed against a balloon, according to illustrative aspects of the present disclosure.

A method for deflating and removing implantable gastric devices is disclosed herein. The method may include pressing distal end 24 of catheter 20 against the wall of a balloon (or other inflatable device), with coring tip 32 refracted, as shown in FIG. 2A-B. By pressing catheter 20 against the balloon wall with coring tip 32 retracted, the user can identify a stable position for the device against the balloon. When pressure is applied to the surface of the balloon by the distal end 24 of catheter 20, the device stretches flat a normalized section of the balloon wall across the distal opening at the distal end 24 of catheter 20, as shown in at least FIG. 3. This normalized section provides a smooth surface conducive to a symmetrical, smooth and circular cut when coring tip 32 is advanced. Furthermore, pushing distal end 24 of catheter 20 against the balloon wall builds up force such that, when the cored opening is made, catheter 20 naturally passes through the cored opening as the balloon wall expands outward. Thus, the opening seals itself around catheter 20 when catheter 20 travels into the balloon, relative to the balloon wall.

Figure 4A:
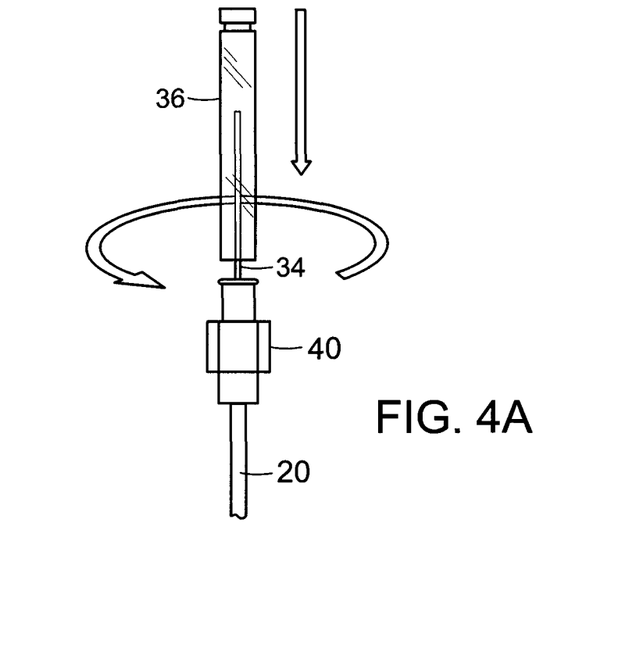
FIG. 4A is a view of embodiments of a proximal portion of a deflation device during a coring phase of operation, according to illustrative aspects of the present disclosure.
Figure 4B:
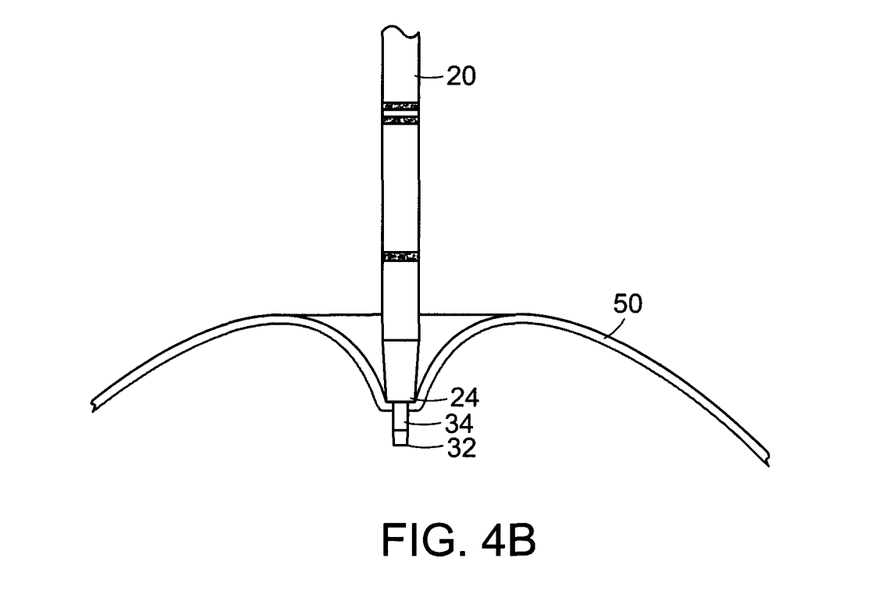
FIG. 4B is a view of embodiments of a distal portion of a deflation device during a coring phase of operation, according to illustrative aspects of the present disclosure.

According to embodiments, coring tip 32 may be advanced beyond distal end 24 of catheter 20, such that coring tip 32 creates a cored opening while distal end 24 of catheter 20 maintains pressure against the wall of the balloon, as shown in at least FIGS. 4A-B. Coring tip 32 may be advanced while being rotated. This rotation may be provided by handle 36 wherein cable 34 transfers a torque to coring tip 32 from handle 36. The combination of pressing coring tip 32 against the balloon wall while rotating coring tip 32 creates a coring action against the balloon wall that forms a smooth, symmetrical, circular cored opening in the balloon.

According to embodiments, longitudinal and/or rotational oscillation (along the length of the coring member) may be provided to coring tip 32 as coring tip 32 creates the cored opening. For example, longitudinal and/or rotational oscillation at a frequency in the ultrasound range may be applied to coring top 32 to facilitate improved coring.

The coring tip may also be advanced into the balloon while applying an energy, such as radiofrequency (RF) hi-frequency electrical energy, to the coring tip. RF energy may be applied via snares, needles, forceps, and the like. According to embodiments, RF energy may be applied to coring tip 32 to heat coring tip 32 and facilitate improved coring.

Figure 5:
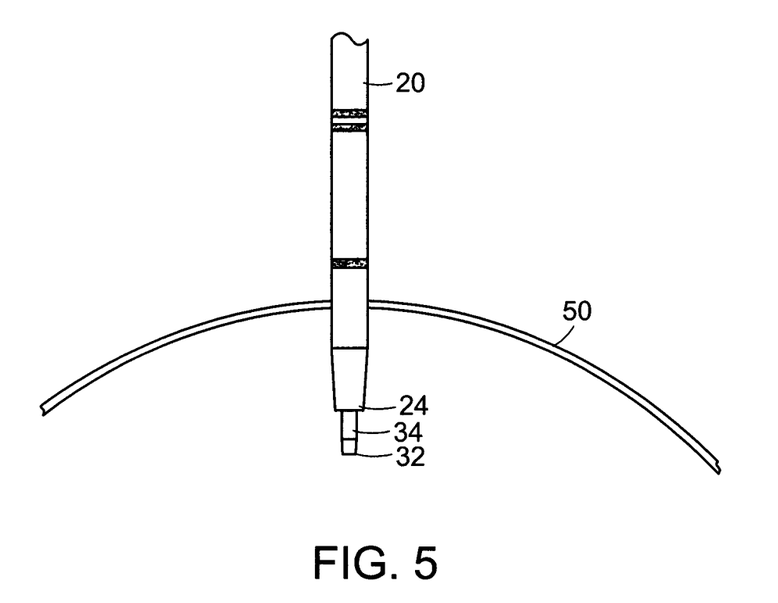
FIG. 5 is a view of embodiments of a distal portion of a deflation device inserted into a balloon, according to illustrative aspects of the present disclosure.
Figure 6A:
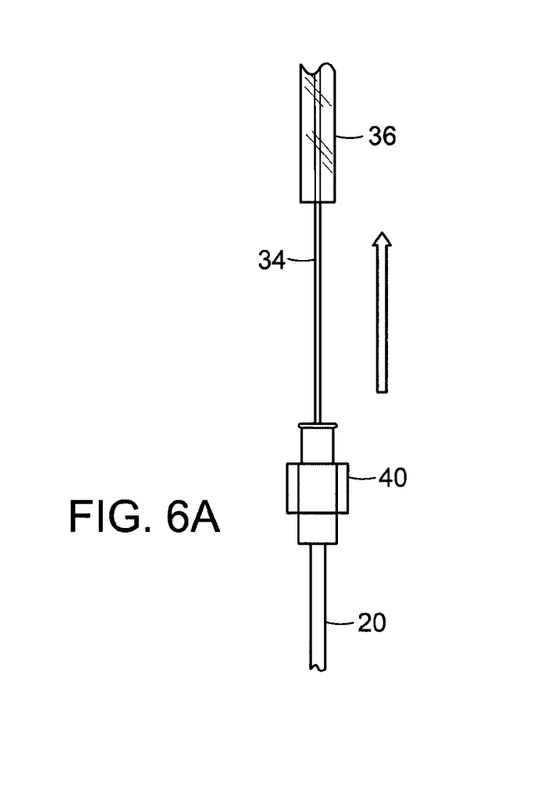
FIG. 6A is a view of embodiments of a proximal portion of a deflation device during a deflation phase of operation, according to illustrative aspects of the present disclosure.
Figure 6B:
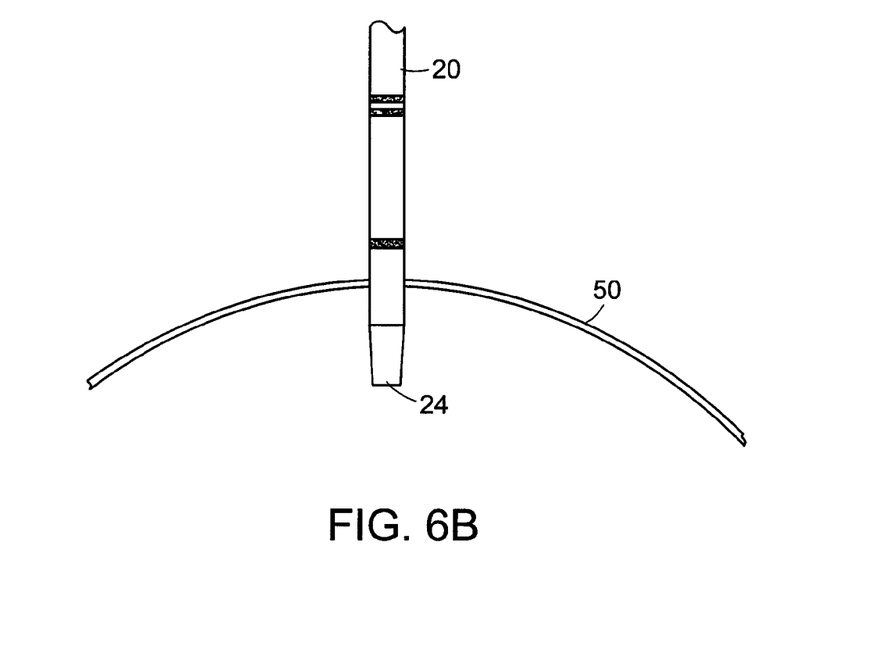
FIG. 6B is a view of embodiments of a distal portion of a deflation device during a deflation phase of operation, according to illustrative aspects of the present disclosure.

According to embodiments, once coring tip 32 has cut through most or the entire balloon wall thickness, the coring member and catheter 20 pass into the balloon, as shown in at least FIG. 5. Once at least distal end 24 of catheter 20 is inside the balloon, the coring member, include coring tip 32, may be retracted along and within catheter 20, as shown in at least FIG. 6A. According to embodiments, coring tip 32 may be completely removed from catheter 20, as shown in at least FIG. 6B. The contents of the balloon, including fluid and solid matter, may be evacuated using a syringe, vacuum pump, or other device to provide relatively lower pressure at proximal end 22 of catheter 20.

According to embodiments, catheter 20 or another catheter/scope may provide a relatively lower pressure to the portion of the outer surface of the balloon wall that is normalized by pressing catheter 20 or another catheter/scope against the balloon wall. The relatively lower pressure applied may further stabilize the area of the cored opening as coring tip 32 passes through the wall of the balloon. Furthermore, the relatively lower pressure applied may help ensure that the portion of the outer surface of the balloon wall that is contacted with coring tip 32 is normalized with respect to coring tip 32.

By employing embodiments of the present disclosure, tearing, leakage, or rupture of balloon is significantly reduced or altogether avoided, preventing excess fluid in the stomach and reducing the risk of fluid aspiration into the trachea. The balloon can be fully evacuated since coring tip 32 creates a cored opening that is substantially smaller in diameter than the outer diameter of catheter 20 and seals around catheter 20 when catheter 20 passes into the balloon. The fully evacuated balloon is much easier to remove and is less likely to create drag in the esophagus.

While the apparatus and method have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an embodiment of any apparatus embodiment, a method or process embodiment, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these disclosure(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 U.S.C. §132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. A method, comprising:
   pressing a distal end of a catheter against a wall of an inflated balloon of an implanted device such that the distal end creates a substantially normalized surface of the balloon; and
   advancing a coring tip from a retracted position within the catheter to an extended position beyond the distal end of the catheter and into the balloon, wherein the coring tip removes a portion of the surface of the balloon to create a substantially circular cored opening through the substantially normalized surface of the balloon.

2. The method of claim 1, wherein the substantially circular cored opening is adapted for receiving the catheter.

3. The method of claim 1 further comprising advancing the catheter through the substantially circular cored opening into the balloon.

4. The method of claim 1, wherein an outer diameter of the catheter forms a seal with the substantially circular cored opening.

5. The method of claim 1 further comprising retracting the coring tip from the catheter.

6. The method of claim 1 further comprising removing contents of the balloon through the catheter.

7. The method of claim 1, wherein the coring tip is advanced into the balloon while applying an external pressure lower than an internal pressure within the balloon, wherein the external pressure is applied at a point of contact between the distal end of the catheter and the wall of the balloon.

8. The method of claim 1, wherein the coring tip is advanced into the balloon while rotating the coring tip.

9. The method of claim 1, wherein the coring tip is advanced into the balloon while delivering energy to the coring tip.

10. The method of claim 9, wherein the energy is a longitudinal oscillation applied at a frequency in the ultrasound range.

11. The method of claim 9, wherein the energy is radiofrequency energy.

12. The method of claim 1, wherein a portion of the wall of the balloon is removed to form the substantially circular cored opening.

13. The method of claim 1, wherein advancing the coring tip includes creating the substantially circular cored opening free of tear propagation points in the wall.

14. A method comprising:
   pressing a distal end of a catheter against a wall of an implanted gastric pressurized balloon, wherein a normalized surface of the wall is formed at a contact point between the distal end and the wall;
   advancing a hole making element from a retracted position within the catheter to an extended position beyond the distal end; and
   cutting a substantially circular hole in the wall of the balloon to remove a portion from the surface of the balloon.

15. The method of claim 14, wherein cutting a substantially circular hole includes separating a substantially circular portion of the wall from the balloon.

16. The method of claim 14, wherein cutting a substantially circular hole includes cutting a hole without forming stress concentration in the wall of the balloon.

17. The method of claim 14, wherein cutting a substantially circular hole includes cutting a hole through the normalized surface.

* * * * *